US012743835B2

(12) United States Patent
Lee et al.

(10) Patent No.: US 12,743,835 B2
(45) Date of Patent: Sep. 22, 2026

(54) SYSTEM AND METHOD FOR CONE-BEAM COMPUTED TOMOGRAPHY IMAGING AND APPARATUS FOR THE SAME

(71) Applicant: Electronics and Telecommunications Research Institute, Daejeon (KR)

(72) Inventors: Soo Yeul Lee, Daejeon (KR); Seung Hoon Chae, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 162 days.

(21) Appl. No.: 18/894,325

(22) Filed: Sep. 24, 2024

(65) Prior Publication Data

US 2025/0173925 A1 May 29, 2025

(30) Foreign Application Priority Data

Nov. 28, 2023 (KR) ........................ 10-2023-0167525

(51) Int. Cl.

| | |
|---|---|
| ***G06T 11/00*** | (2026.01) |
| ***A61B 6/00*** | (2006.01) |
| ***A61B 6/03*** | (2006.01) |
| ***A61B 6/40*** | (2024.01) |
| ***A61B 6/58*** | (2024.01) |
| ***G06T 12/20*** | (2026.01) |

(52) U.S. Cl.

CPC .............. *G06T 12/20* (2026.01); *A61B 6/032* (2013.01); *A61B 6/4085* (2013.01); *A61B 6/4441* (2013.01); *A61B 6/583* (2013.01); *G06T 2211/421* (2013.01)

(58) Field of Classification Search

None

See application file for complete search history.

(56) References Cited

U.S. PATENT DOCUMENTS

| | | | | |
|---|---|---|---|---|
| 8,478,007 | B2 | 7/2013 | Lee et al. | |
| 10,311,602 | B2 | 6/2019 | Choi et al. | |
| 10,925,572 | B1 * | 2/2021 | Chang | A61B 6/583 |
| 10,952,694 | B2 | 3/2021 | Son et al. | |

(Continued)

FOREIGN PATENT DOCUMENTS

| | | |
|---|---|---|
| KR | 10-2018-0082027 A | 7/2018 |
| KR | 10-2022-0169669 A | 12/2022 |

OTHER PUBLICATIONS

Gao, Juan, et al. "A projection matrix-based geometric calibration algorithm in CBCT system." *2017 10th International Congress on Image and Signal Processing, BioMedical Engineering and Informatics* (*CISP-BMEI*). IEEE, 2017.

(Continued)

*Primary Examiner* — Marcus H Taningco

(74) *Attorney, Agent, or Firm* — NSIP Law

(57) ABSTRACT

The present disclosure relates to a cone beam computed tomography (CT) imaging system, an image processing method, and a device therefor. An image processing method performed by a cone beam computed tomography (CT) imaging apparatus including a source and a detector that rotate around an object may include: obtaining a plurality of projection images projected on the detector for the object; obtaining a correction projection matrix; and reconstructing a three-dimensional image by back-projecting the plurality of projection images based on the correction projection matrix.

13 Claims, 10 Drawing Sheets

(56) References Cited

U.S. PATENT DOCUMENTS

| | | | | |
|---|---|---|---|---|
| 11,669,961 | B2 | 6/2023 | Jung et al. | |
| 2004/0252811 | A1* | 12/2004 | Morita | A61B 6/583 378/207 |

OTHER PUBLICATIONS

Graetz, Jonas. "Auto-calibration of cone beam geometries from arbitrary rotating markers using a vector geometry formulation of projection matrices." Physics in Medicine & Biology 66.7 (2021): 075013. arXiv:1808.03337v2 [eess.IV], Aug. 20, 2020. (pp. 1-23).

Li, Xinhua, Da Zhang, and Bob Liu. "A generic geometric calibration method for tomographic imaging systems with flat-panel detectors—A detailed implementation guide." Medical physics 37.7 Part1, Jun. 29, 2010. (pp. 3844-3854).

* cited by examiner

FPI
Fiber Optic
Orbital Drive
Host PC
E FG CAN
Display
CAN1
FPI Controller
Trigger
X-ray Tube
Generator
Int. Host
Controller
CAN2
Foot Pedal

SYSTEM AND METHOD FOR CONE-BEAM COMPUTED TOMOGRAPHY IMAGING AND APPARATUS FOR THE SAME

CROSS-REFERENCE TO RELATED APPLICATIONS

This application claims the benefit of earlier filing date and right of priority to Korean Application No. 10-2023-0167525, filed on Nov. 28, 2023, the contents of which are all hereby incorporated by reference herein in their entirety.

TECHNICAL FIELD

The present disclosure relates to an image processing method, and more specifically, to a cone beam computed tomography (CT) imaging system including a source and a detector that rotate around an object, an image processing method, and a device therefor.

BACKGROUND

A cone-beam computed tomography (CBCT) system includes an X-ray source and an X-ray detector. The X-ray source and the X-ray detector can acquire multiple two-dimensional projection images while rotating around an object. In order to generate a three-dimensional image of the object from the acquired two-dimensional projection images, the positional relationship for the X-ray source, the X-ray detector and the object at the time of acquiring the projection images must be accurately determined. If the positional relationship the X-ray source, the X-ray detector and the object is not accurately determined, the clarity of the three-dimensional image of the object may deteriorate.

In a cone beam CT system, a gantry, which is a frame that supports an X-ray source and an X-ray detector to acquire an X-ray image on an object, can rotate along an orbit. If the rotational trajectory of the gantry can be accurately determined, the positional relationship for the X-ray source, the X-ray detector and the object can be accurately determined. However, it is difficult to accurately determine the rotation trajectory of the gantry due to structural sagging of the gantry or deformation of the rotation trajectory, and it is very difficult to accurately determine the positional relationship for the X-ray source, the X-ray detector and the object. Accordingly, the clarity of the three-dimensional image of the subject may deteriorate.

SUMMARY

In conventional cone beam CT imaging systems, projection matrices are mainly calculated from projection images of geometric calibration phantoms and used in the back-projection process of 3D cone beam CT image reconstruction. However, the flat-panel X-ray detector used in cone beam CT has parallax depending on the position in reading the image signal, which can cause errors in the projection matrix when using a high-speed rotating cone beam CT system or a high-magnification cone beam CT system, resulting in deterioration of the image quality of sophisticated 3D reconstruction images.

A technical object of the present disclosure is to provide a cone beam CT imaging system, an image processing method, and a device therefor that improves the image quality of a three-dimensional image by correcting an error of a projection matrix caused by the image output parallax of a flat X-ray detector.

The technical objects to be achieved by the present disclosure are not limited to the above-described technical objects, and other technical objects which are not described herein will be clearly understood by those skilled in the pertinent art from the following description.

An image processing method performed by a cone beam computed tomography (CT) imaging apparatus including a source and a detector that rotate around an object may include: obtaining a plurality of projection images projected on the detector for the object; obtaining a correction projection matrix; and reconstructing a three-dimensional image by back-projecting the plurality of projection images based on the correction projection matrix. The obtaining the correction projection matrix may include: obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

A cone beam computed tomography (CT) imaging apparatus including a source and a detector that rotate around an object may include: at least one processor; and at least one memory operably connected to the at least one processor and storing instructions that, when executed by the one or more processors, cause the apparatus to perform operations for image processing. The operations may include: obtaining a plurality of projection images projected on the detector for the object; obtaining a correction projection matrix; and reconstructing a three-dimensional image by back-projecting the plurality of projection images based on the correction projection matrix. The obtaining the correction projection matrix may include: obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

At least one non-transitory computer-readable medium storing at least one instruction, wherein the at least one instruction executable by at least one processor may control a cone beam computed tomography (CT) imaging apparatus including a source and a detector that rotate around an object to: obtain a plurality of projection images projected on the detector for the object; obtain a correction projection matrix; and reconstruct a three-dimensional image by back-projecting the plurality of projection images based on the correction projection matrix. The obtaining the correction projection matrix may include: obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

Preferably, after calculating a projection matrix by assigning the weight to the specific component to each of the center coordinates of the plurality of beads, the component-weighted projection matrix may be obtained by dividing a row of the projection matrix that affect the specific component by the weight.

Preferably, the correction projection matrix may be obtained by separately using the component-weighted projection matrix for each component.

Preferably, the correction projection matrix may be obtained by combining a plurality of component-weighted projection matrices obtained for each component.

Preferably, the correction projection matrix may be obtained by extracting and combining one or more rows from each of the plurality of component-weighted projection matrices.

Preferably, the component-weighted projection matrix may be obtained using a singular value decomposition (SVD) scheme.

According to an embodiment of the present disclosure, an error in a projection matrix caused by a parallax in an image output of a flat detector can be corrected.

In addition, according to an embodiment of the present disclosure, by correcting an error of a projection matrix, a more accurate projection matrix can be obtained, thereby preventing deterioration of image quality of a 3-dimensional (3D) reconstructed image.

Effects achievable by the present disclosure are not limited to the above-described effects, and other effects which are not described herein may be clearly understood by those skilled in the pertinent art from the following description.

BRIEF DESCRIPTION OF THE DRAWINGS

Accompanying drawings included as part of detailed description for understanding the present disclosure provide embodiments of the present disclosure and describe technical features of the present disclosure with detailed description.

DETAILED DESCRIPTION

Figures 1, 2:
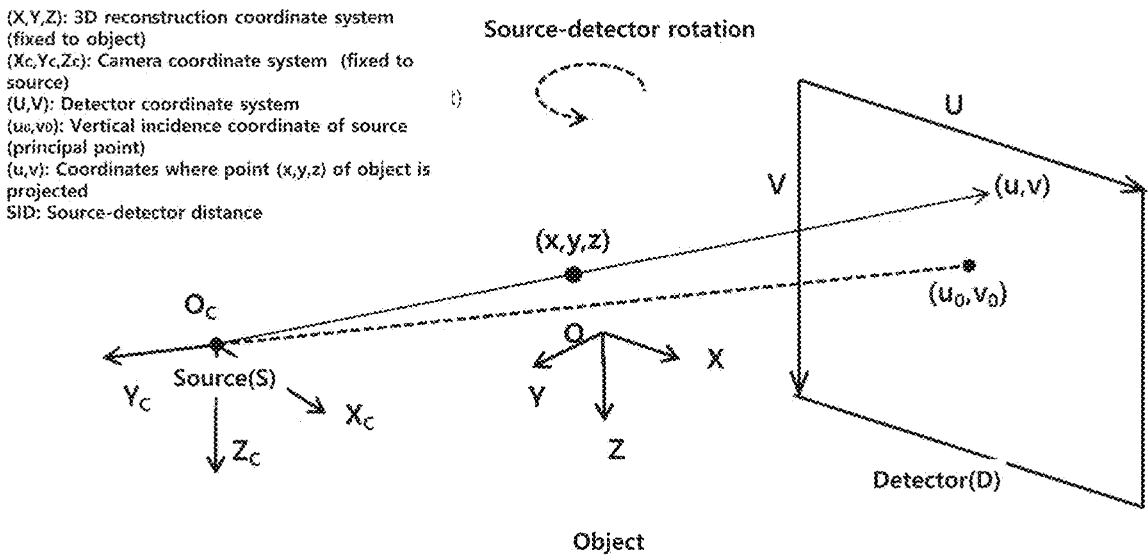
FIG. 1 illustrates a cone-beam computed tomography (CT) imaging system to which the present invention can be applied.
FIG. 2 illustrates a general C-arm imaging system to which the present invention can be applied.

Since the present disclosure can make various changes and have various embodiments, specific embodiments will be illustrated in the drawings and described in detail in the detailed description. However, this is not intended to limit the present disclosure to specific embodiments, and should be understood to include all changes, equivalents, and substitutes included in the feature and technical scope of the present disclosure. Similar reference numbers in the drawings refer to identical or similar functions across various aspects. The shapes and sizes of elements in the drawings may be exaggerated for clearer explanation. For a detailed description of the exemplary embodiments described below, refer to the accompanying drawings, which illustrate specific embodiments by way of example. These embodiments are described in sufficient detail to enable those skilled in the art to practice the embodiments. It should be understood that the various embodiments are different from one another but are not necessarily mutually exclusive. For example, specific shapes, structures and characteristics described herein with respect to one embodiment may be implemented in other embodiments without departing from the spirit and scope of the disclosure. Additionally, it should be understood that the position or arrangement of individual components within each disclosed embodiment may be changed without departing from the spirit and scope of the embodiment. Accordingly, the detailed description that follows is not to be intended in a limiting sense, and the scope of the exemplary embodiments is limited only by the appended claims, together with all equivalents to what those claims assert if properly described.

In the present disclosure, terms such as first, second, etc. may be used to describe various components, but the components should not be limited by the terms. The above terms are used only for the purpose of distinguishing one component from another. For example, a first component may be referred to as a second component, and similarly, the second component may be referred to as a first component without departing from the scope of the present disclosure. The term "and/or" includes any of a plurality of related stated items or a combination of a plurality of related stated items.

When a component of the present disclosure is referred to as being "connected" or "accessed" to another component, it may be directly connected or connected to the other component, but other components may exist in between. It must be understood that it may be possible. On the other hand, when it is mentioned that a component is "directly connected" or "directly accessed" to another component, it should be understood that there are no other components in between.

The components appearing in the embodiments of the present disclosure are shown independently to represent different characteristic functions, and do not mean that each component is comprised of separate hardware or one software component. That is, each component is listed and included as a separate component for convenience of explanation, and at least two of each component can be combined to form one component, or one component can be divided into a plurality of components to perform a function, and each of these components can be divided into a plurality of components. Integrated embodiments and separate embodiments of the constituent parts are also included in the scope of the present disclosure as long as they do not deviate from the essence of the present disclosure.

The terms used in this disclosure are only used to describe specific embodiments and are not intended to limit the disclosure. Singular expressions include plural expressions unless the context clearly dictates otherwise. In the present disclosure, terms such as "comprise" or "have" are intended to designate the presence of features, numbers, steps, operations, components, parts, or combinations thereof described in the specification, but are not intended to indicate the presence of one or more other features. It should be understood that this does not exclude in advance the possibility of the existence or addition of elements, numbers, steps, operations, components, parts, or combinations thereof. In other words, the description of "including" a specific configuration in this disclosure does not exclude configurations other than the configuration, and means that additional configurations may be included in the scope of the implementation of the disclosure or the technical feature of the disclosure.

Some of the components of the present disclosure may not be essential components that perform essential functions in the present disclosure, but may simply be optional components to improve performance. The present disclosure can be implemented by including only essential components for implementing the essence of the present disclosure, excluding components used only to improve performance, and a structure that includes only essential components excluding optional components used only to improve performance. is also included in the scope of rights of this disclosure.

Hereinafter, embodiments of the present disclosure will be described in detail with reference to the drawings. In describing the embodiments of the present specification, if it is determined that a detailed description of a related known configuration or function may obscure the gist of the present specification, the detailed description will be omitted, and the same reference numerals will be used for the same components in the drawings. Redundant descriptions of the same components are omitted.

FIG. 1 illustrates a cone-beam computed tomography (CT) imaging system to which the present invention can be applied.

Referring to FIG. 1, a typical cone-beam CT (computed tomography) imaging system may be composed of a structure (gantry) including an X-ray source and a flat panel X-ray detector that rotate around an object. In a cone-beam CT, multiple 2-dimensional (2D) projection images are acquired by rotating the source(S) and detector (D) with individual coordinate systems around the object. In the present disclosure, rotation is relative concept, i.e., x-ray source and detector can rotate actively around an object or an object itself can rotate. In order to reconstruct the acquired 2D projection images into a 3D image, each 2D projection image is filtered and then the image is back-projected according to the arrangement relationship of the X-ray source, detector, and reconstruction space at the time of acquisition of the projection images. The back-projection is the process of reprojecting values in pixels (u, v) of the detector in the direction of the X-ray source.

Here, it is necessary to know the exact arrangement relationship of the X-ray source, detector, and reconstruction space, and their arrangement relationship can generally be determined from the arrangement design of the X-ray source and detector and the information of the controller driving it. If the arrangement relationship between the X-ray source, detector, and reconstruction space is determined inaccurately, an error occurs in the back-projection process, which reduces the clarity of the reconstructed 3D image. However, the arrangement of components in the system design and the arrangement information provided by the controller may differ from the actual due to device deformation, controller accuracy, and measurement parallax of the arrangement information.

FIG. 2 illustrates a general C-arm imaging system to which the present invention can be applied.

In particular, when implementing a cone beam CT function in a C-arm device such as FIG. 2, structural sagging or deformation of the gantry is likely to occur, so it is necessary to precisely determine the arrangement relationship between the source, detector, and reconstruction space through actual measurements rather than design.

Figure 3:
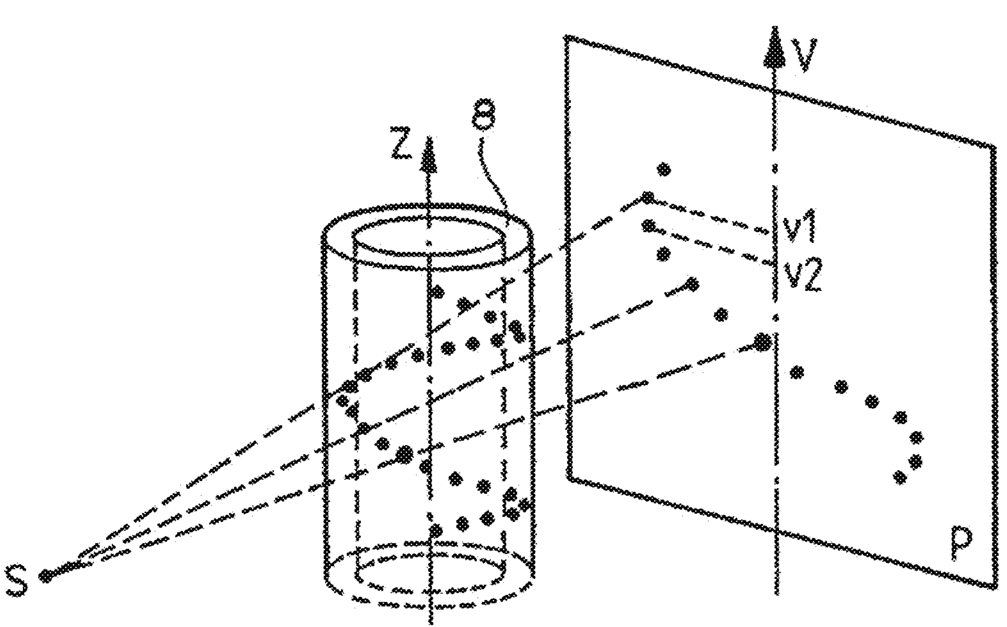
FIG. 3 illustrates a CT geometric calibration phantom composed of helical beads.

FIG. 3 illustrates a CT geometric calibration phantom composed of helical beads.

There are several methods to determine the geometric arrangement of a cone beam CT. Generally, X-ray images of a specially manufactured calibration phantom with a number of metal beads whose 3D coordinates are precisely known are acquired, and then a projection matrix (PM) that defines the relationship between the already known 3D bead coordinates and the coordinates projected onto a 2D plane is obtained to determine the geometric arrangement of the cone beam CT system, and this is used for back-projection.

The projection matrix (PM) is a 3×4 matrix, and with reference to the coordinate relationship in FIG. 1, it satisfies following Equations 1 and 2. That is, PM refers to a 3×4 matrix that configures the ray matching relationship between the point (x, y, z) in the reconstruction space and the point (u, v) on the detector. When reconstructing CT images, it is very efficient because the back-projection position (x, y, z) can be simply calculated from the detector coordinates (u, v).

$$-y_C\begin{pmatrix} u \\ v \\ 1 \end{pmatrix} = PM\begin{pmatrix} x \\ y \\ z \\ 1 \end{pmatrix} \quad \text{[Equation 1]}$$

$$-y_C u = P_{11}x + P_{12}y + P_{13}z + P_{14} \quad \text{[Equation 2]}$$

$$-y_C v = P_{21}x + P_{22}y + P_{23}z + P_{24}$$

$$-y_C = P_{31}x + P_{32}y + P_{33}z + P_{34}$$

Here, (x, y, z) are spatial coordinates in the 3D reconstruction coordinate system (X-axis, Y-axis, Z-axis), and x, y, z represent coordinate values for the X-axis, Y-axis, and Z-axis, respectively (i.e., coordinate values for the point of the object). (u, v) are spatial coordinates of the projected point (x, y, z) of the object in the detector coordinate system (U-axis, V-axis), and u, v represent coordinate values for the U-axis and V-axis, respectively.

$P_{11}$~$P_{34}$ are 12 elements that compose a 3×4 projection matrix, and $y_C$ is a proportional constant (i.e., scale factor) that is calculated for each spatial coordinate (x, y, z).

If the scale factor $y_C$ is removed from Equation 2, it can be expressed as Equation 3 below.

$$u(P_{31}x + P_{32}y + P_{33}z + P_{34}) = P_{11}x + P_{12}y + P_{13}z + P_{14} \quad \text{[Equation 3]}$$

$$v(P_{31}x + P_{32}y + P_{33}z + P_{34}) = P_{21}x + P_{22}y + P_{23}z + P_{24}$$

Each element of P can be calculated using the position of each bead (i.e., (x, y, z)) and the bead projection position in the detector coordinate system (i.e., (u, v)). In other words, the bead coordinates (x, y, z) in the three-dimensional space in the reconstruction coordinate system fixed to the calibration phantom are mapped to the detector coordinates (u, v) by imaging with X-rays, and the mapping relationship is defined by PM and the Equation 1.

More specifically, using the bead positions [(u,v), (x,y,z)] of the X-ray image, a homogeneous equation for $P_{11}$~$P_{34}$ is generated, and P can be determined by considering P as a 12-dimensional vector and calculating it. Here, the number of required formulas is 12 or more (the minimal number of bead points is 6), and the coefficient matrix M (m×n, m>=n, n=12) is determined by this. Here, if SVD is applied to M, $M=UDV^T$. U represents an orthogonal matrix composed of orthonormal eigenvectors (i.e., left singular vectors) of $MM^T$, and V represents an orthogonal matrix composed of orthonormal eigenvectors (i.e., right singular vectors) of $M^TM$, and D represents a diagonal matrix whose diagonal elements are non-negative, and whose diagonal elements are the square roots of the eigenvalues of $M^TM$. Here, according to the SVD theory, the solution of MP=0 corresponds to the right singular vector whose eigenvalue is 0 in $M^TM$. Meanwhile, P can be normalized using the condition that the norm of ($P_{31}$, $P_{32}$, $P_{33}$)=1. Using P, $y_C$ is determined for any (x, y, z), and (u, v) is also determined.

When PM is calculated accurately as above, the back-projection position relationship is accurately defined, so the 3D reconstruction image is clear.

Figure 4:
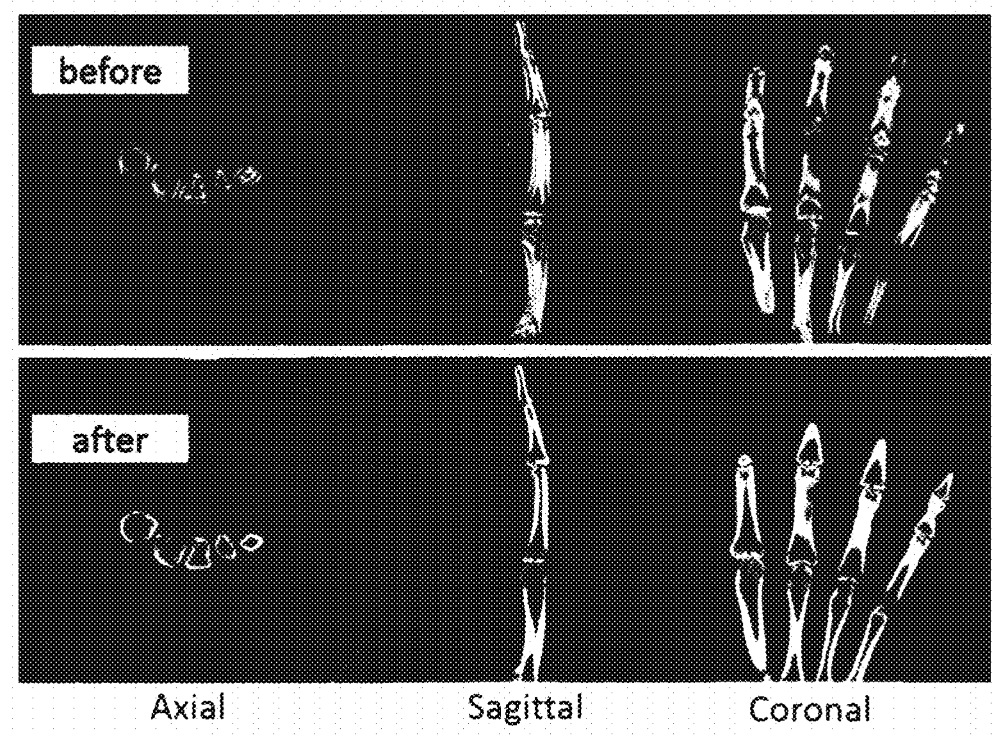
FIG. 4 illustrates a 3D CT image reconstructed using a projection image obtained from a C-arm-based cone-beam system.

FIG. 4 illustrates a 3D CT image reconstructed using a projection image obtained from a C-arm-based cone-beam system.

FIG. 4(*a*) is a tomographic image of a 3D reconstruction image of a hand phantom that was performed by identifying the arrangement relationship of the source and detector using the design information of the cone-beam system and the gantry rotation angle provided by the controller, and FIG. 4(*b*) is a tomographic image of a 3D reconstruction image of a hand phantom that was performed using the PM obtained by imaging a calibration bead phantom.

As can be seen in the image, the tomographic image of the 3D reconstruction image using PM is more accurate and clearer than that using only the system design information and the gantry rotation angle information. This is a phenomenon that occurs because there is a significant difference between the motion trajectory of the C-arm system design and the actual C-arm motion trajectory.

Figure 5:
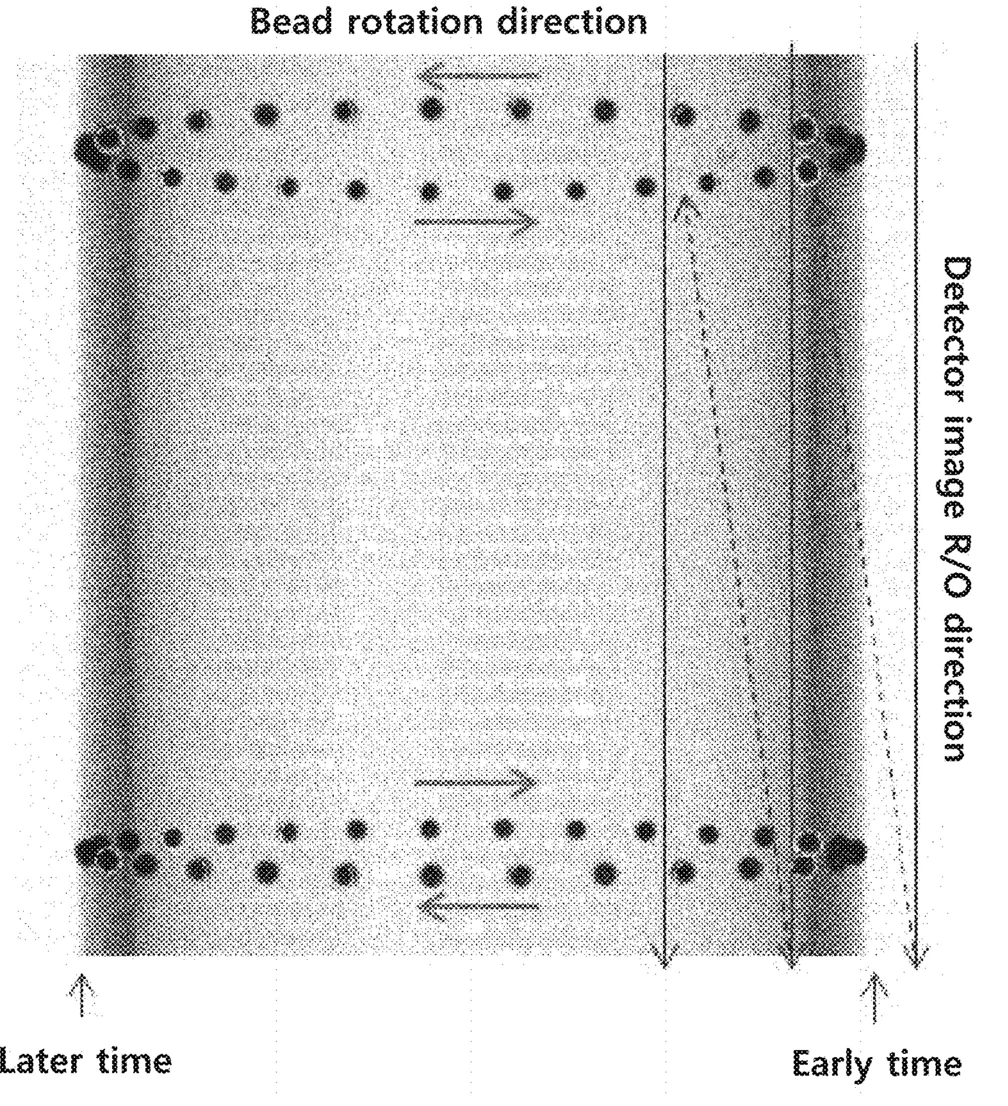
FIG. 5 illustrates an effect due to parallax in an image output from an image of a calibration phantom in which two rows of metal beads are arranged on a circle.

FIG. 5 illustrates an effect due to parallax in an image output from an image of a calibration phantom in which two rows of metal beads are arranged on a circle.

Meanwhile, referring to FIG. 5, the flat-panel X-ray detector outputs images based on frames, however since it takes time to output one frame image (R/O: readout), there is a time difference in the image output for each detector position, which causes a slight time difference in the X-ray exposure timing. Here, if the gantry rotation is slow, there is no problem, however if the gantry rotation is fast or the magnification of the subject is large, the position where the bead is formed (i.e., u, v in Equation 1) includes significant changes depending on the slight time difference in the X-ray exposure timing for each pixel of the detector. The dotted circle in FIG. 5 indicates the expected projection position of the bead when the R/O time is 0, and the actual projected position of the bead can be seen to be outside the dotted circle. In such cases, a significant error occurs in the projection matrix (PM) calculated based on Equations 2 and 3. If a 3D cone beam CT image is reconstructed using the projection matrix containing such an error, an error is expected in the 3D reconstructed image.

Figure 6:
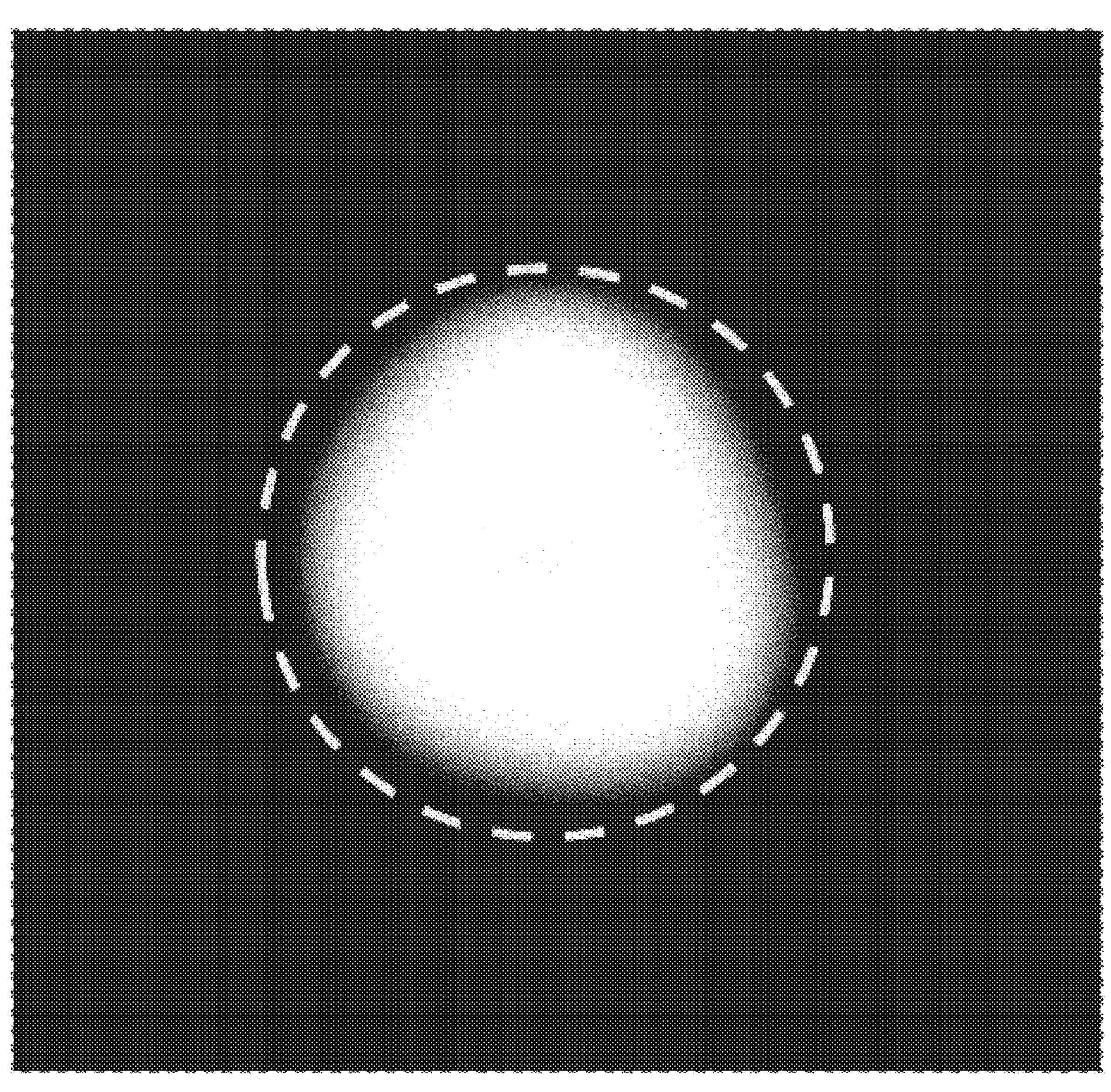
FIG. 6 illustrates a 3D reconstructed image of a calibration phantom bead portion.

FIG. 6 illustrates a 3D reconstructed image of a calibration phantom bead portion.

FIG. 6 shows an example of the 3D reconstruction result using the X-ray image of the calibration phantom, and it can be confirmed that the outer shape of the metal ball attached to the phantom (the white sphere) is slightly different from a perfect sphere (dotted line).

Currently, the cone beam CTs mainly used do not have fast gantry rotation or the magnification of the object is not large, so the error occurring in PM is negligible, however medical cone beam CTs are also expected to evolve to a high-speed rotation method, and magnification photography of tens to hundreds of times is already common in industrial component inspection, and the demand for high-speed rotation imaging is also increasing, therefore the error occurring in PM is becoming a situation where it cannot be ignored in 3D image quality.

Based on the above-described content, a method for correcting errors in the projection matrix of the present invention is described. The above-described content can be combined with the content of the present invention proposed below, even if not mentioned separately.

As described above, in order to calculate the projection matrix (PM), the center coordinates (u,v) of the metal beads can be obtained from the image of the geometric calibration phantom containing N metal beads, as shown in FIG. 5, and the precise 3D spatial coordinates (x,y,z) of each metal bead can be obtained through the design information of the calibration phantom or actual measurement. The N (x,y,z)-(u,v) pairs obtained in this way are substituted into the Equation 3 to obtain 2N equations. Here, at least 12 equations are required. The 12 unknowns ($P_{11}$ to $P_{34}$) in the 2N equations constitute a 3×4 projection matrix, which can be calculated using the singular value decomposition (SVD) scheme. Here, the result of the singular value decomposition corresponding to the singular value of 0 (i.e., when the eigenvalue of $M^TM$ is 0) corresponds to the desired projection matrix.

Here, if there is a parallax in the image output (R/O) of the detector, there may be a problem that the center coordinates (u, v) of the bead obtained from the projection image may have a systematic error depending on the position on the detector. As in the example of FIG. 5, when the image output of the detector proceeds in the column direction, errors mainly occur in the u-value (i.e., errors on the U-axis), and errors in the v-value (i.e., errors on the V-axis) rarely occur. In addition, the error directions of the u-values of the beads on the detector side and the beads on the X-ray source side based on the rotation axis of the calibration phantom are opposite to each other. For this reason, the calculation of the projection matrix using the center (u, v) of the bead obtained from the projection image and the three-dimensional coordinates (x, y, z) of the bead includes a systematic error.

Figure 7:
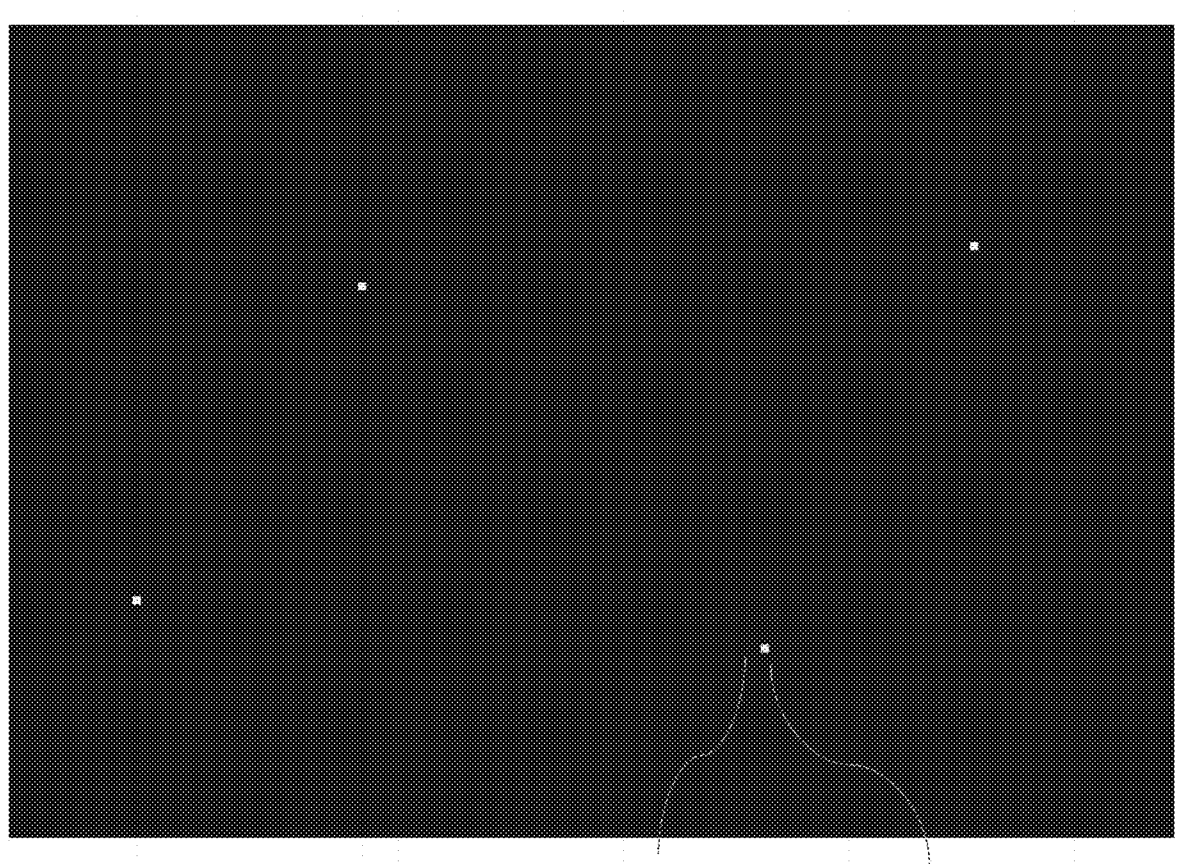
FIG. 7 illustrates an error between a bead center position calculated by projecting a bead with a conventional projection matrix (PM) and a bead center position calculated by image processing from a projection image.

FIG. 7 illustrates an error between a bead center position calculated by projecting a bead with a conventional projection matrix (PM) and a bead center position calculated by image processing from a projection image.

Referring to FIG. 7, the white dot at the center of the bead is the center found by precise image processing in the projection image, and the gray dot is the projected center of the bead coordinates (x, y, z) by the projection matrix containing errors. In normal cases, there is a sub-pixel level discrepancy between the center points calculated by the two methods (usually less than 0.3 pixels), but in cases where there is a projection matrix error due to the image output parallax, a discrepancy of more than 1 pixel may occur.

When the object is projected onto a detector plane without image output parallax by a point-based X-ray source, a precise projection matrix is calculated. However, if there is a detector image output parallax as in FIG. 5, it gives the effect that the X-ray source is not a point.

To be more specific, the error in the center of the bead on the detector occurs depending on the rotation of the gantry, and the error in the center of the bead can mostly occur in the U-axis direction (because the gantry including the source-detector rotates around an axis that is almost parallel to the V-axis). In an ideal case, the positions of the bead phantom and various parameters can be determined so that the lines ($I_1, I_2, I_3 \ldots I_N$) passing through the corresponding bead centers (x, y, z) on the phantom from the actual bead centers (u, v) on the detector converge on one source(S) (this process corresponds to the singular value decomposition by Equation 3 described above).

Here, if the axis perpendicular to the U-axis and V-axis of the detector is called the W-axis, in real situations, the convergence pattern of the straight lines ($I_1^{uw}$, $I_2^{uw}$, $I_3^{uw} \ldots I_N^{uw}$) projected onto the UW plane is different from the convergence pattern of the straight lines ($I_1^{vw}$, $I_2^{vw}$, $I_3^{vw} \ldots I_N^{vw}$) projected onto the vw plane. In the vw plane projection, they converge almost exactly to one point ($S^{vw}$), and in the UW plane projection, they converge approximately to one point ($S^{uw}$). However, $S^{vw}$ almost exactly matches S based on the vw plane projection, and $S^{uw}$ becomes closer or farther from the detector than S depending on the rotation direction/speed of the gantry, the image output direction/speed of the detector, etc. based on the UW plane projection.

Since the projection matrix only needs to precisely provide the relationship in which the 3D coordinates (x, y, z) on the object are projected to the 2D coordinates (u, v) on the detector for a given imaging setting (gantry rotation direction/speed, detector frame rate, source-detector distance (SID: Source Image Receptor Distance), source-gantry rotation center distance (SOD: Source Object Distance), etc.), practical projection matrix error correction is possible as follows, considering the characteristics of UW plane projection and vw plane projection as explained above.

In the example of FIG. 5, the weight of u can be increased and the projection matrix ($PM_u$) can be calculated by SVD (Singular Value Decomposition). In this way, the X-ray source can be calculated to be farther away than it actually is. More specifically, among the beads that appear on the upper and lower ellipses of the projection image, the beads that appear relatively large are located closer to the X-ray source, so if the weight of u is increased and SVD is performed, the u value is matched first, so the light source can be recognized to be farther away than it actually is. Then, if the beads are projected with the calculated projection matrix $PM_u$, the results as in FIG. 8 can be obtained.

Figure 8:
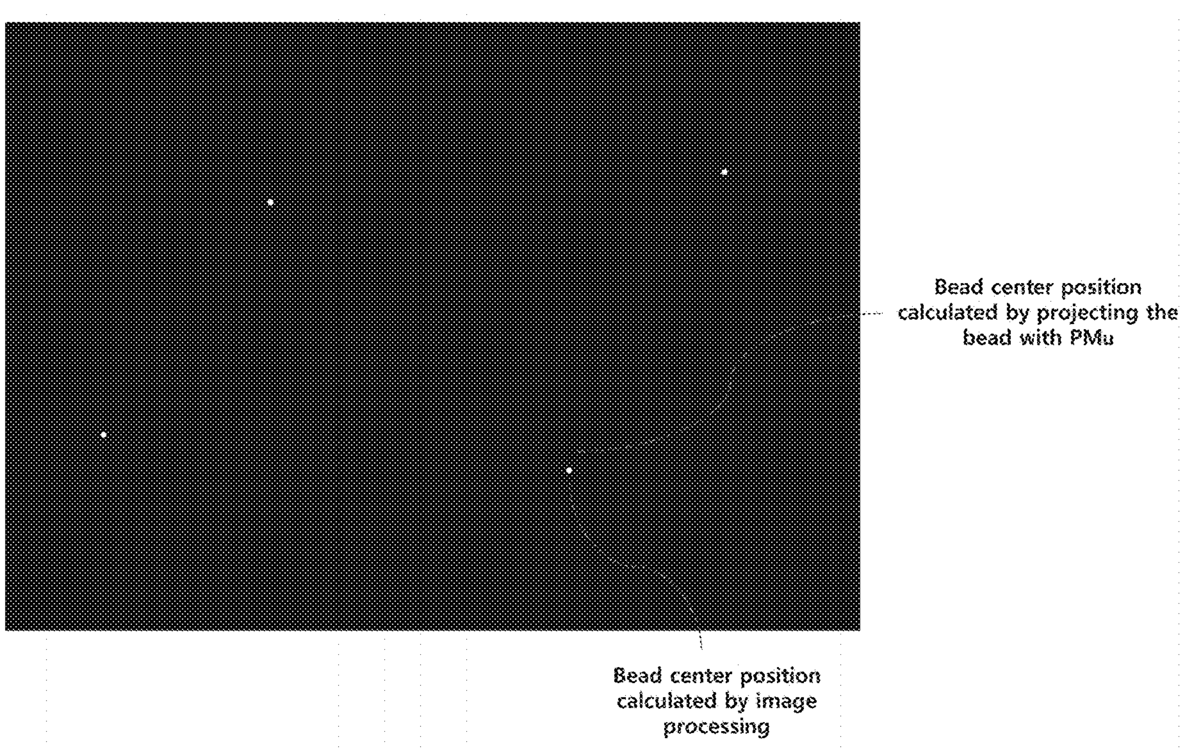
FIG. 8 illustrates an error between a bead center position calculated by projecting a bead with a U-component weighted projection matrix (PMu) according to an embodiment of the present invention and a bead center position calculated by image processing in a projection image.

FIG. 8 illustrates an error between a bead center position calculated by projecting a bead with a U-component weighted projection matrix ($PM_u$) according to an embodiment of the present invention and a bead center position calculated by image processing in a projection image.

Referring to FIG. 8, the white dot at the center of the bead is the center found through precise image processing in the projection image, and the gray dot is the center projected with the bead coordinates (x, y, z) using a weighted projection matrix ($PM_u$).

In order to weight u, a method can be used in which the projection matrix is calculated by SVD by multiplying the u value by a scale greater than 1, and then dividing the rows of the projection matrix that affect u in Equation 1 by the scale. FIG. 8 illustrates the result of $PM_u$ obtained by setting the scale to 10. In other words, the result of calculating PM by weighting u by 10 times (i.e., multiplying by 10) is illustrated. Here, the weight of 10 corresponds to a value illustrated for convenience of explanation, and the present invention is not limited thereto, and a value greater than 1 or less than 1 can be used as the weight. If a value less than 1 is given as a weight to the u value, the effect of giving a weight greater than 1 to the v component can be obtained.

Figure 9:
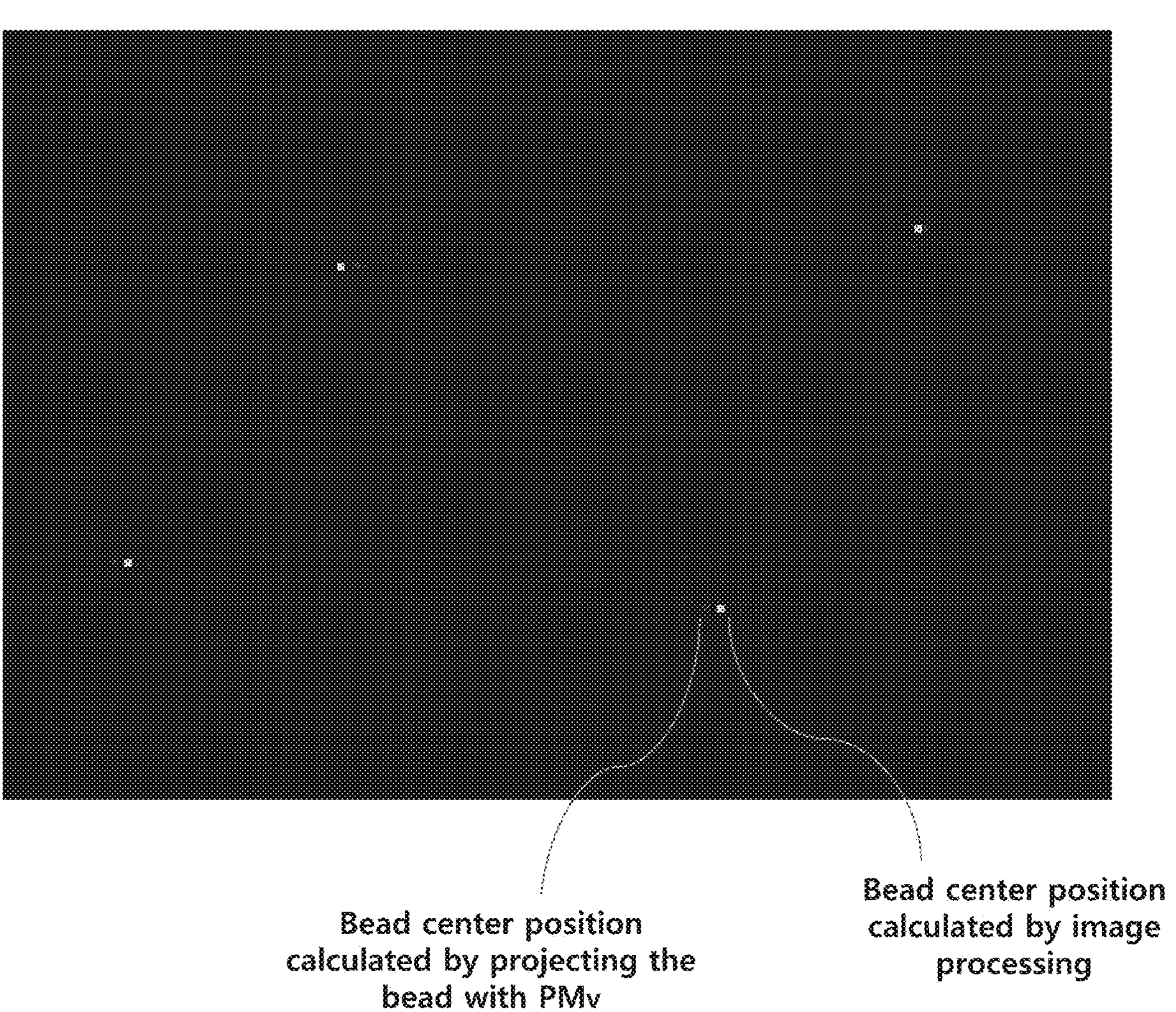
FIG. 9 illustrates an error between a bead center position calculated by projecting a bead with a V-component weighted projection matrix (PMv) according to an embodiment of the present invention and a bead center position calculated by image processing in a projection image.

Meanwhile, the result of calculating the projection matrix ($PM_v$) using SVD by increasing the weight of v is as shown in FIG. 9.

FIG. 9 illustrates an error between a bead center position calculated by projecting a bead with a V-component weighted projection matrix ($PM_v$) according to an embodiment of the present invention and a bead center position calculated by image processing in a projection image.

FIG. 9 illustrates the result of $PM_v$ obtained by setting the scale to 10. That is, it illustrates the result of calculating PM by weighting v by 10 times (i.e., multiplying by 10). Here, the weight of 10 corresponds to a value illustrated for convenience of explanation, and the present invention is not limited thereto, and a value greater than 1 or less than 1 may be used as the weight. If a value less than 1 is given as a weight to the v value, the effect of giving a weight greater than 1 to the u component can be obtained.

As shown in FIGS. 8 and 9, as expected, the result by $PM_u$ prioritizes u, and the result by $PM_v$ prioritizes v.

In order to obtain a more accurate 3×4 projection matrix between (u,v) and (x,y,z), a 3×4 component-weighted projection matrix ($PM_u$ and $PM_v$) that calculates u and v independently can be obtained and used as a component-wise correction projection matrix as in Equations 4 and 5 below. In other words, by using two PMs, the u-direction and v-direction components can be separately and preferentially matched.

$$k_u\begin{pmatrix} u \\ v \\ 1 \end{pmatrix} = PM_u\begin{pmatrix} x \\ y \\ z \\ 1 \end{pmatrix} \quad \text{[Equation 4]}$$

$$k_v\begin{pmatrix} u \\ v \\ 1 \end{pmatrix} = PM_v\begin{pmatrix} x \\ y \\ z \\ 1 \end{pmatrix} \quad \text{[Equation 5]}$$

Here, in order to derive $PM_u$ and $PM_v$, the method described in Equations 1 to 3 above can be used, but the weights of u and v can be adjusted, respectively. In other words, 12 or more relationships are obtained using 6 or more different beads, (x, y, z)-(u, v) pair information and Equation 3, and PM is calculated through singular value decomposition (SVD), and when calculating $PM_u$, the coefficient matrix M can be derived using Equation 3 and multiple bead coordinate values [(u, v), (x, y, z)] information multiplied by a scale value by a predetermined (or set) size to the u value.

Then, the final $PM_u$ can be derived by dividing the scale value in the row (i.e., the first row) that affects the u value in the coefficient matrix M (i.e., multiplying by 1/(scale value)).

Similarly, when calculating $PM_v$, the coefficient matrix M can be derived using the information of multiple bead coordinate values [(u,v), (x,y,z)] multiplied by the scale value by a predetermined (or set) size to the v value and the Equation 3. Then, the final $PM_v$ can be derived by dividing the scale value in the row (i.e., the second row) that affects the v value in the coefficient matrix M (i.e., multiplying by 1/(scale value)).

Meanwhile, the 3×4 component-weighted projection matrix ($PM_u$ and $PM_v$) that calculates u and v independently can be simplified to use the 2×4 component-weighted projection matrix ($PM_u^{(2\times4)}$ and $PM_v^{(2\times4)}$ as in Equations 6 and 7. $PM_u^{(2\times4)}$ in Equation 6 is $PM_u$ with the second row removed, and $PM_v^{(2\times4)}$ in Equation 7 is $PM_v$ with the first row removed.

$$k_u\begin{pmatrix} u \\ 1 \end{pmatrix} = PM_u^{(2\times4)}\begin{pmatrix} x \\ y \\ z \\ 1 \end{pmatrix} \quad \text{[Equation 6]}$$

$$k_v\begin{pmatrix} v \\ 1 \end{pmatrix} = PM_v^{(2\times4)}\begin{pmatrix} x \\ y \\ z \\ 1 \end{pmatrix} \quad \text{[Equation 7]}$$

Additionally, $PM_u$ and $PM_v$ can be combined into a 4×4 combined correction projection matrix ($PM_n$) as in Equation 8 below.

$$\begin{pmatrix} k_u\begin{pmatrix} u \\ 1 \end{pmatrix} \\ k_v\begin{pmatrix} v \\ 1 \end{pmatrix} \end{pmatrix} = PM_n\begin{pmatrix} x \\ y \\ z \\ 1 \end{pmatrix} \quad \text{[Equation 8]}$$

Here, the combined correction projection matrix can be generated as a 4×4 matrix $PM_n$ by combining a 2×4 matrix consisting of $1^{st}$ and $3^{rd}$ rows of $PM_u$ used in computing u and $k_u$ and a 2×4 matrix consisting of $2^{nd}$ and $3^{rd}$ rows of $PM_v$ used in computing v and $k_v$.

Figure 10:
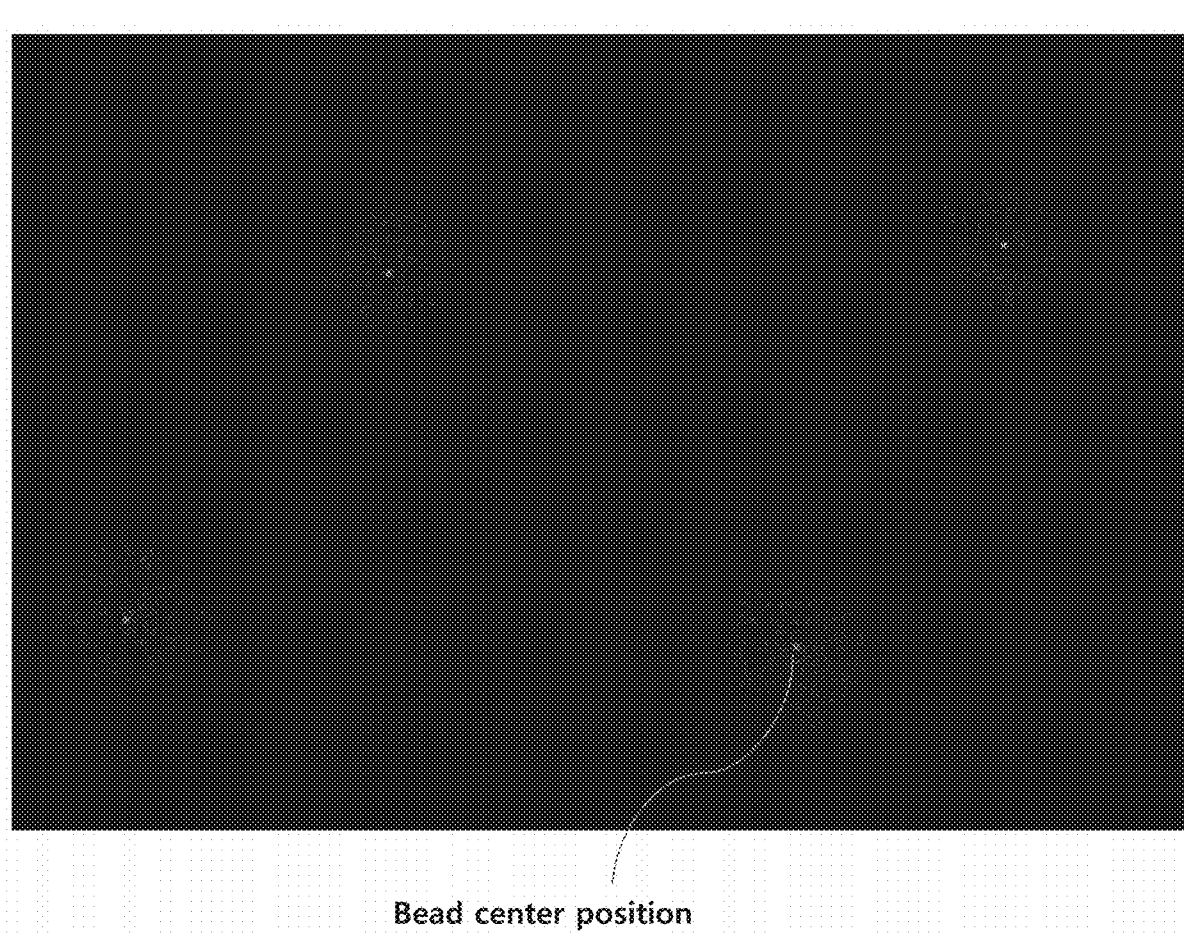
FIG. 10 illustrates an error between a bead center position calculated by projecting a bead with a correction projection matrix according to an embodiment of the present invention.

FIG. 10 illustrates an error between a bead center position calculated by projecting a bead with a correction projection matrix according to an embodiment of the present invention.

FIG. 10 illustrates the bead center position calculated by the component-wise correction projection matrix according to the Equations 4 (or 6) and 5 (or 7) or the combined correction projection matrix according to the Equation 8. The bead center found by image processing is identical at the pixel level, therefore the two center points appear to overlap as one.

Figure 11:
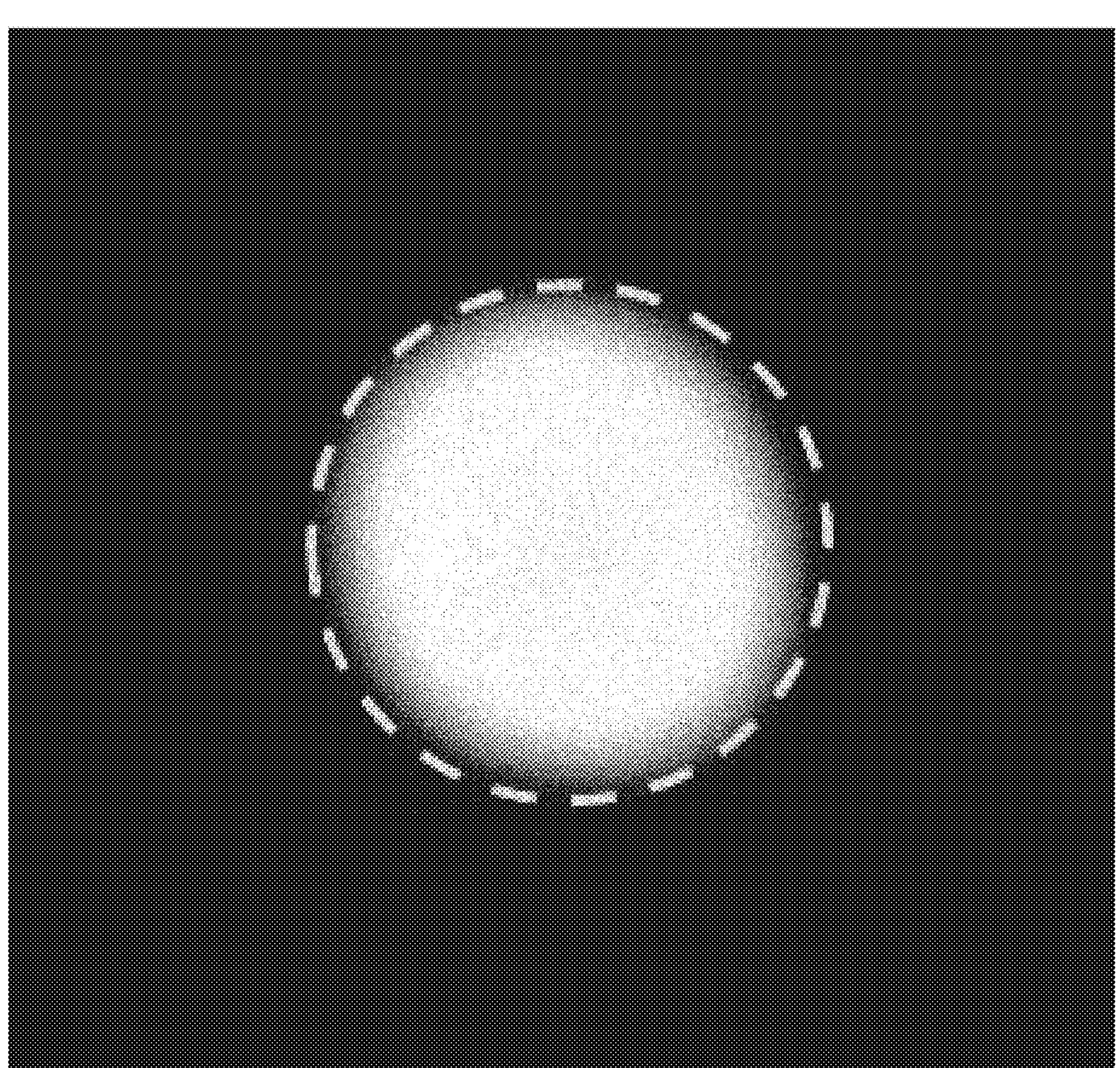
FIG. 11 illustrates an image of a 3D reconstructed image of a calibration phantom bead portion with a correction projection matrix according to an embodiment of the present invention.

FIG. 11 illustrates an image of a 3D reconstructed image of a calibration phantom bead portion with a correction projection matrix according to an embodiment of the present invention.

Referring to FIG. 11, it can be confirmed that the distorted sphere of FIG. 6 is almost restored by the correction projection matrix.

In the present invention, a more sophisticated cone beam CT imaging system that corrects the error of the projection matrix caused by the image output parallax of the flat panel detector is proposed, and this can be utilized in the future to improve the image quality of 3D reconstruction images by coping with the image output parallax of the flat panel detector in a medical high-speed cone beam CT imaging system or an industrial cone beam CT system requiring high magnification/high-speed imaging.

Figure 12:
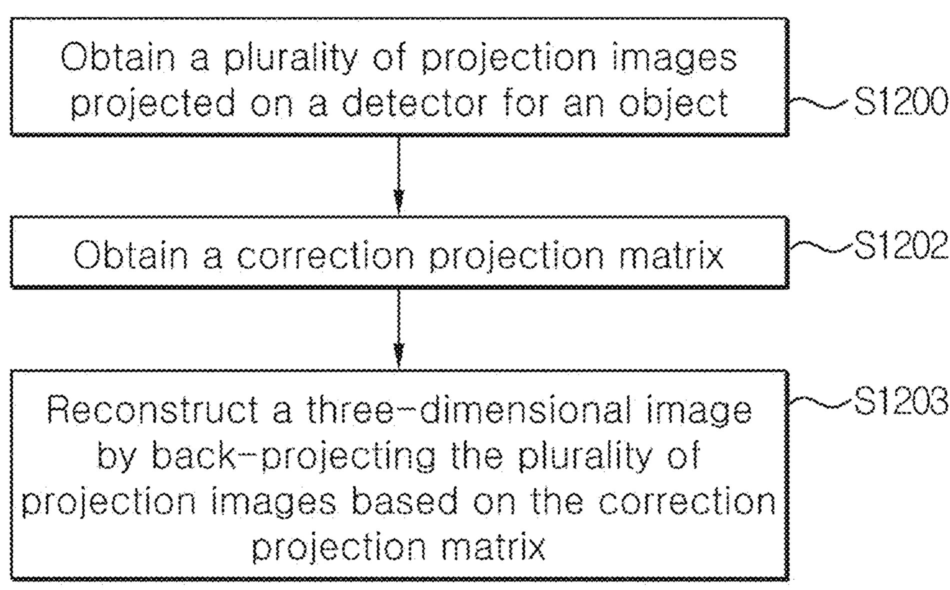
FIG. 12 illustrates an image processing method according to an embodiment of the present invention.

FIG. 12 illustrates an image processing method according to an embodiment of the present invention.

Referring to FIG. 12, a cone beam CT imaging apparatus including a source and a detector that rotate around an object acquires a plurality of projection images projected on the detector for the object (S1201).

Here, the apparatus can perform filtering to remove noise, etc. with respect to the plurality of projection images projected on the detector.

The apparatus acquires a correction projection matrix (S1202).

The correction projection matrix can be acquired based on the method described above.

For example, the apparatus can first obtain spatial coordinates for the plurality of beads from a geometric calibration phantom to which a plurality of beads are attached, and center coordinates for each of the plurality of beads from a projection image projected onto a detector for the geometric calibration phantom. In addition, the apparatus can obtain a correction projection matrix based on a component-weighted projection matrix obtained by assigning a weight to each center coordinate of a plurality of beads for a specific component. Here, the component-weighted projection matrix can be obtained by calculating the projection matrix by assigning a weight to specific components to each center coordinate for multiple beads, and then dividing the rows of the projection matrix affecting a specific component by the weight. In addition, the correction projection matrix can be obtained by separately using the component-weighted projection matrix for each component, and accordingly, the component-weighted projection matrix for a specific component can be regarded as the correction projection matrix. In addition, the correction projection matrix can be obtained by combining multiple component-weighted projection matrices obtained for each component. Here, as described above, one or more rows are extracted from each of a plurality of component-weighted projection matrices, and the extracted rows are combined to obtain the component-weighted projection matrix. In addition, the component-weighted projection matrix can be obtained using the singular value decomposition (SVD) scheme.

The apparatus reconstructs a three-dimensional image by back-projecting a plurality of projection images based on a correction projection matrix (S1203).

Figure 13:
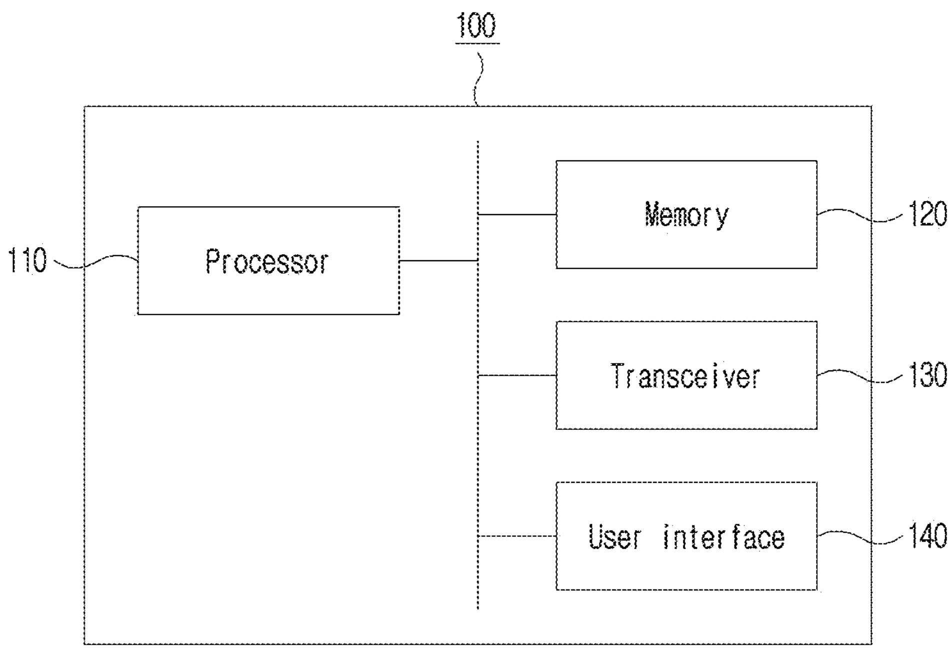
FIG. 13 is a block diagram of an image processing device according to an embodiment of the present disclosure.

FIG. 13 is a block diagram of an image processing apparatus according to an embodiment of the present disclosure.

The image processing apparatus of FIG. 13 may correspond to a cone beam CT imaging apparatus including a source and detector that rotate around an object.

The image processing apparatus (100) may include one or more processors (110), one or more memories (120), one or more transceivers (130), and one or more user interfaces (140). The memory (120) may be included in the processor (110) or may be configured separately. The memory (120) may store instructions that, when executed by the processor (110), cause the apparatus (100) to perform an operation. The transceiver (130) may transmit and/or receive signals and data that the apparatus (100) exchanges with other entities. The user interface (140) may receive a user's input regarding the apparatus (100) or provide an output of the apparatus (100) to the user. Among the components of the apparatus (100), components other than the processor (110) and the memory (120) may not be included in some cases, and other components not shown in FIG. 13 may be included in the apparatus (100).

The processor (110) may be configured to enable the above-described image processing apparatus (100) to perform methods according to various examples of the present disclosure. Although not shown in FIG. 13, the processor (110) may be configured as a set of modules that perform each method/function proposed in this disclosure. Modules may be configured in hardware and/or software form.

The processor (110) acquires a plurality of projection images projected on the detector for the object (S1201). Here, the processor (110) can perform filtering to remove noise, etc. with respect to the plurality of projection images projected on the detector.

The processor (110) acquires a correction projection matrix. The correction projection matrix can be acquired based on the method described above.

For example, the processor (110) can first obtain spatial coordinates for the plurality of beads from a geometric calibration phantom to which a plurality of beads are attached, and center coordinates for each of the plurality of beads from a projection image projected onto a detector for the geometric calibration phantom. In addition, the processor (110) can obtain a correction projection matrix based on a component-weighted projection matrix obtained by assigning a weight to each center coordinate of a plurality of beads for a specific component. Here, the component-weighted projection matrix can be obtained by calculating the projection matrix by assigning a weight to specific components to each center coordinate for multiple beads, and then dividing the rows of the projection matrix affecting a specific component by the weight. In addition, the correction projection matrix can be obtained by separately using the component-weighted projection matrix for each component, and accordingly, the component-weighted projection matrix for a specific component can be regarded as the correction projection matrix. In addition, the correction projection matrix can be obtained by combining multiple component-weighted projection matrices obtained for each component. Here, as described above, one or more rows are extracted from each of a plurality of component-weighted projection matrices, and the extracted rows are combined to obtain the component-weighted projection matrix. In addition, the component-weighted projection matrix can be obtained using the singular value decomposition (SVD) scheme.

The processor (110) reconstructs a three-dimensional image by back-projecting a plurality of projection images based on a correction projection matrix.

Components described in exemplary embodiments of the present disclosure may be implemented by hardware elements. For example, the hardware element may include at least one of a digital signal processor (DSP), a processor, a controller, an application specific integrated circuit (ASIC), a programmable logic element such as an FPGA, a GPU, other electronic devices, or a combination thereof. At least some of the functions or processes described in the exemplary embodiments of the present disclosure may be implemented as software, and the software may be recorded on a recording medium. Components, functions, and processes described in exemplary embodiments may be implemented in a combination of hardware and software.

The method according to an embodiment of the present disclosure may be implemented as a program that can be executed by a computer, and the computer program may be recorded in various recording media such as magnetic storage media, optical read media, and digital storage media.

The various technologies described in this disclosure may be implemented as digital electronic circuits or computer hardware, firmware, software, or a combination thereof. The above technologies may be implemented as a computer program product, that is, a computer program tangibly embodied in an information medium (e.g., a machine-readable storage device (e.g., a computer-readable medium) or a data processing device) or a computer program implemented as signals processed by or propagated by a data processing device to cause the operation of the data processing device (e.g., programmable processor, computer, or multiple computers).

Computer program(s) may be written in any form of programming language, including compiled or interpreted languages and may be distributed as a stand-alone program or in any form, including modules, components, subroutines, or other units suitable for use in a computing environment. A computer program may be executed by a single computer or by multiple computers distributed at one site or multiple sites and interconnected by a communications network.

Examples of processors suitable for executing computer programs include general-purpose and special-purpose microprocessors, and one or more processors in digital computers. Typically, a processor receives instructions and data from read-only memory, random access memory, or both. Components of a computer may include at least one processor for executing instructions and one or more memory devices for storing instructions and data. Additionally, the computer may include one or more mass storage devices for data storage, such as magnetic, magneto-optical disks, or optical disks, or may be connected to the mass storage devices to receive and/or transmit data. Examples of information media suitable for implementing computer program instructions and data include optical media such as semiconductor memory devices (e.g., magnetic media such as hard disks, floppy disks, and magnetic tapes), compact disk read-only memory (CD-ROM), digital video disk (DVD), etc., magneto-optical media such as floptical disks, and read only memory (ROM), random access memory (RAM), flash memory, erasable programmable ROM (EPROM), electrically erasable programmable ROM (EEPROM), and other known computer-readable media. Processors and memories can be supplemented or integrated by special-purpose logic circuits.

A processor may run an operating system (OS) and one or more software applications that run on the OS. The processor device may also access, store, manipulate, process and generate data in response to software execution. For simplicity, the processor device is described in the singular, but those skilled in the art will understand that the processor device may include a plurality of processing elements and/or various types of processing elements. For example, a processor device may include a plurality of processors or a processor and a controller. Additionally, different processing structures, such as parallel processors, may be configured. Additionally, computer-readable media refers to all media that a computer can access, and may include both computer storage media and transmission media.

Although this disclosure includes detailed descriptions of various detailed implementation examples, the details should not be construed as limiting the invention or scope of the claims proposed in this disclosure, but rather illustrating features of specific exemplary embodiments.

Features individually described in exemplary embodiments in this disclosure may be implemented by a single exemplary embodiment. Conversely, various features described in this disclosure with respect to a single exemplary embodiment may be implemented by a combination or appropriate sub-combination of a plurality of exemplary embodiments. Furthermore, in the present disclosure, the features may operate by a specific combination, and the combination may initially be described as claimed, however, in some cases, one or more features may be excluded from the claimed combination, or claimed combinations may be modified in the form of sub-combinations or modifications of sub-combinations.

Similarly, even if operations are depicted in a specific order in the drawings, it should not be understood that execution of the operations in a specific order or sequence is necessary, or that performance of all operations is required to obtain a desired result. In certain cases, multitasking and parallel processing can be useful. Additionally, it should not be understood that the various device components in all exemplary embodiments are necessarily separate, and the above-described program components and devices may be packaged in a single software product or multiple software products.

The exemplary embodiments disclosed herein are illustrative only and are not intended to limit the scope of the disclosure. Those skilled in the art will recognize that various modifications may be made to the exemplary embodiments without departing from the scope of the claims and their equivalents.

Accordingly, this disclosure is intended to include all other substitutions, modifications and changes that fall within the scope of the following claims.

What is claimed is:

1. An image processing method performed by a cone beam computed tomography (CT) imaging apparatus including a source and a detector that rotate around an object, the method comprising:

obtaining a plurality of projection images projected on the detector for the object;

obtaining a correction projection matrix; and reconstructing a three-dimensional image by back-projecting the plurality of projection images based on the correction projection matrix, wherein the obtaining the correction projection matrix comprising:

obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

2. The method of claim 1, wherein after calculating a projection matrix by assigning the weight to the specific component to each of the center coordinates of the plurality of beads, the component-weighted projection matrix is obtained by dividing a row of the projection matrix that affect the specific component by the weight.

3. The method of claim 2, wherein the correction projection matrix is obtained by separately using the component-weighted projection matrix for each component.

4. The method of claim 2, wherein the correction projection matrix is obtained by combining a plurality of component-weighted projection matrices obtained for each component.

5. The method of claim 4, wherein the correction projection matrix is obtained by extracting and combining one or more rows from each of the plurality of component-weighted projection matrices.

6. The apparatus of claim 2, wherein the component-weighted projection matrix is obtained using a singular value decomposition (SVD) scheme.

7. A cone beam computed tomography (CT) imaging apparatus including a source and a detector that rotate around an object, the apparatus comprising:

at least one processor; and at least one memory operably connected to the at least one processor and storing instructions that, when executed by the one or more processors, cause the apparatus to perform operations for image processing comprising:

obtaining a plurality of projection images projected on the detector for the object;

obtaining a correction projection matrix; and reconstructing a three-dimensional image by back-projecting the plurality of projection images based on the correction projection matrix, wherein the obtaining the correction projection matrix comprising:

obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

8. The apparatus of claim 7, wherein after calculating a projection matrix by assigning the weight to the specific component to each of the center coordinates of the plurality of beads, the component-weighted projection matrix is obtained by dividing a row of the projection matrix that affect the specific component by the weight.

9. The apparatus of claim 8, wherein the correction projection matrix is obtained by separately using the component-weighted projection matrix for each component.

10. The apparatus of claim 8, wherein the correction projection matrix is obtained by combining a plurality of component-weighted projection matrices obtained for each component.

11. The apparatus of claim 10, wherein the correction projection matrix is obtained by extracting and combining one or more rows from each of the plurality of component-weighted projection matrices.

12. The apparatus of claim 8, wherein the component-weighted projection matrix is obtained using a singular value decomposition (SVD) scheme.

13. At least one non-transitory computer-readable medium storing at least one instruction, wherein the at least one instruction executable by at least one processor controls a cone beam computed tomography (CT) imaging apparatus including a source and a detector that rotate around an object to:

obtain a plurality of projection images projected on the detector for the object;

obtain a correction projection matrix; and reconstruct a three-dimensional image by back-projecting the plurality of projection images based on the correction projection matrix, wherein the obtaining the correction projection matrix comprising:

obtaining spatial coordinates for a plurality of beads in a geometric calibration phantom with the plurality of beads and each of the center coordinates for the plurality of beads from a projection image projected on the detector for the geometric calibration phantom; and obtaining the correction projection matrix based on a component-weighted projection matrix obtained by assigning a weight to a specific component to each of the center coordinates of the plurality of beads.

* * * * *